US012623990B2

(12) United States Patent
Straussner et al.

(10) Patent No.: US 12,623,990 B2
(45) Date of Patent: May 12, 2026

(54) METHODS FOR IMPROVED CONTROL OF GLACIAL ACETIC ACID PROCESSES

(71) Applicant: LyondellBasell Acetyls, LLC, Houston, TX (US)

(72) Inventors: Austin R. Straussner, Houston, TX (US); Shane J. Weber, League City, TX (US); Noel C. Hallinan, Loveland, OH (US); David A. Heaps, Pearland, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 471 days.

(21) Appl. No.: 18/319,059

(22) Filed: May 17, 2023

(65) Prior Publication Data

US 2023/0375478 A1 Nov. 23, 2023

Related U.S. Application Data

(60) Provisional application No. 63/343,690, filed on May 19, 2022.

(51) Int. Cl.
| | |
|---|---|
| *C07C 51/12* | (2006.01) |
| *B01J 19/00* | (2006.01) |
| *C07C 53/08* | (2006.01) |
| *G01N 21/65* | (2006.01) |
| *G01N 21/35* | (2014.01) |

(52) U.S. Cl.
CPC .......... *C07C 51/12* (2013.01); *B01J 19/0006* (2013.01); *C07C 53/08* (2013.01); *G01N 21/65* (2013.01); *G01N 2021/3595* (2013.01)

(58) Field of Classification Search
CPC ...... C07C 51/12; C07C 53/08; B10J 19/0006; G01N 21/65; G01N 2021/3595
See application file for complete search history.

(56) References Cited

U.S. PATENT DOCUMENTS

| | | | |
|---|---|---|---|
| 3,492,283 | A | 1/1970 | Miller |
| 3,772,156 | A | 11/1973 | Johnson et al. |
| 4,039,395 | A | 8/1977 | Eby |

(Continued)

FOREIGN PATENT DOCUMENTS

| | | |
|---|---|---|
| EP | 487284 A2 | 5/1992 |
| WO | 9511485 A1 | 4/1995 |

(Continued)

OTHER PUBLICATIONS

The International Search Report and The Written Opinion for PCT/US2023/022524 mailed Aug. 2, 2023.

*Primary Examiner* — Yate' K Cutliff

(57) ABSTRACT

Methods and systems for measuring component concentrations. The methods may include providing a system configured for contacting a first component, a second component, and a third component; determining a concentration of the second component in a reactor; determining a concentration of the third component in the reactor; determining a temperature and a pressure of a first apparatus downstream of the reactor; and calculating a first concentration of the first component in the reactor based on (i) the concentration of the second component in the reactor, (ii) the concentration of the third component in the reactor, and (iii) the temperature and the pressure of the first apparatus.

15 Claims, 5 Drawing Sheets

(56)                  References Cited

U.S. PATENT DOCUMENTS

| 4,102,922 | A | 7/1978 | Price |
|---|---|---|---|
| 5,227,520 | A | 7/1993 | Cooper |
| 5,371,286 | A | 12/1994 | Blay et al. |
| 5,416,237 | A | 5/1995 | Aubigne et al. |
| 5,599,976 | A | 2/1997 | Scates et al. |
| 5,625,095 | A | 4/1997 | Miura et al. |
| 5,723,660 | A | 3/1998 | Morimoto et al. |
| 5,783,731 | A | 7/1998 | Fisher et al. |
| 5,831,120 | A | 11/1998 | Watson et al. |
| 5,916,422 | A | 6/1999 | Kimura et al. |
| 6,103,934 | A | 8/2000 | Hallinan et al. |
| 6,362,366 | B1 | 3/2002 | Hallinan et al. |
| 6,552,221 | B1 * | 4/2003 | Hallinan ............... B01J 19/128 |
|  |  |  | 562/517 |
| 8,519,182 | B2 | 8/2013 | Salisbury et al. |
| 9,302,975 | B1 | 4/2016 | Shaver et al. |
| 9,656,939 | B2 | 5/2017 | Hallinan et al. |
| 10,118,884 | B2 | 11/2018 | Hallinan et al. |
| 10,227,283 | B2 | 3/2019 | Hallinan et al. |
| 2012/0022289 | A1 | 1/2012 | Hallinan et al. |
| 2016/0137575 | A1 * | 5/2016 | Liu ......................... C07C 51/48 |
|  |  |  | 562/517 |
| 2016/0264502 | A1 * | 9/2016 | Hallinan ............ G01N 21/3577 |
| 2017/0210690 | A1 * | 7/2017 | Hallinan ................ G01N 21/65 |
| 2019/0284379 | A1 | 9/2019 | Kniesel et al. |

FOREIGN PATENT DOCUMENTS

| WO | 9817619 | A2 | 4/1998 |
|---|---|---|---|
| WO | 9822420 | A1 | 5/1998 |

* cited by examiner

METHODS FOR IMPROVED CONTROL OF GLACIAL ACETIC ACID PROCESSES

CROSS-REFERENCE TO RELATED APPLICATIONS

The application claims the benefit of priority to U.S. Provisional Patent Application No. 63/343,690, filed on May 19, 2022, which is incorporated herein by reference in its entirety.

FIELD OF THE INVENTION

This disclosure relates to the production of acetic acid. More particularly, the disclosure relates to methods for controlling the production of acetic acid.

BACKGROUND

In some glacial acetic acid processes, maintaining a steady state reactor methyl acetate concentration can depend on one or more variables, such as methanol feed, carbon monoxide feed, and/or active catalyst, e.g., rhodium, concentration.

For processes operating at a methyl acetate reactor concentration of greater than 3 wt. %, a mis-match of any of methyl acetate's dependent variables, in some instances, can cause methyl acetate concentration to increase rapidly, thereby increasing the likelihood of significant disturbances in downstream equipment and plant trips.

Several different methods have been devised to perform direct or indirect methyl acetate measurement. As reactor methyl acetate generally correlates inversely with decanter heavy phase density, one method relies on an on-line heavy phase density measurement to calculate reactor methyl acetate concentration. This method, however, has several disadvantages. For example, due to the fact that the decanter is downstream of the reactor, there is a time lag. The method is a reactive, not a proactive, technique. Other reactive methods for controlling methyl acetate concentration include controlling carbon monoxide flow rate in response to temperature.

Some methods directly measure reactor methyl acetate and other reactor components in real time via Fourier transform infrared spectroscopy (FTIR) and Raman spectroscopy (see, e.g., U.S. Pat. Nos. 6,103,934; 6,362,366; 8,519,182; and 10,227,283). These methods typically use either flow through cells or in-situ probes. Although these methods can contribute to improved process control, they can face one or more difficulties.

For example, in both the near infrared (NIR FTIR) and Raman spectra of reactor solutions, the methyl acetate peak at least partially overlaps with other peaks, which can adversely impact the accuracy of a measurement. As an additional example, random signal fluctuation in Raman spectra can result in a need for normalization in order to prevent over- or under-prediction of component concentrations (see, e.g., U.S. Pat. Nos. 9,656,939; and 10,118,884).

There remains a need for methods for directly or indirectly measuring one or more reactor components, such as methyl acetate, including reliable methods that measure methyl acetate in real time so that upward and/or downward trends in methyl acetate concentration can be identified quickly.

SUMMARY OF THE INVENTION

An aspect of the disclosure relates to methods for measuring one or more reactor components, including methods in which pseudo-analyzers or surrogate analyzers are used as (i) a cross-check of FTIR and/or Raman analyzer data, or (ii) an independent method of real time calculation of various reactor component concentrations.

An aspect of the present disclosure relates to methods for calculating a concentration of a first component in a reactor based on (i) a concentration of a second component in the reactor, (ii) a concentration of a third component in the reactor, and (iii) the temperature and the pressure of a first apparatus downstream of the reactor.

Yet another aspect of the present disclosure relates to methods that include providing a system configured for contacting a first component, a second component, and a third component, wherein the system includes a reactor, and a first apparatus downstream of the reactor; determining a concentration of the second component in the reactor; determining a concentration of the third component in the reactor; determining a temperature and a pressure of the first apparatus; and calculating a first concentration of the first component in the reactor based on (i) the concentration of the second component in the reactor, (ii) the concentration of the third component in the reactor, and (iii) the temperature and the pressure of the first apparatus.

Additional aspects will be set forth in part in the description which follows, and in part will be obvious from the description, or may be learned by practice of the aspects described herein. The advantages described herein will be realized and attained by means of the elements and combinations particularly pointed out in the appended claims. It is to be understood that both the foregoing general description and the following detailed description are exemplary and explanatory and are not restrictive.

BRIEF DESCRIPTION OF THE DRAWINGS

The claimed subject matter may be understood by reference to the following description taken in conjunction with the accompanying drawings, in which like reference numerals identify like elements, and in which:

While the disclosed process, method and system are susceptible to various modifications and alternative forms, the drawings illustrate specific embodiments herein described in detail by way of example. It should be understood, however, that the description herein of specific embodiments is not intended to limit the invention to the particular forms disclosed, but on the contrary, the intentions is to cover all modifications, equivalents, and alternatives falling within the spirit and scope of the invention as defined by the appended claims.

DETAILED DESCRIPTION

A detailed description of embodiments of the disclosed process and method follows. However, it is to be understood that the described embodiments are merely exemplary of the process and method and that the process and method may each be embodied in various and alternative forms of the described embodiments. Therefore, specific procedural, structural and functional details which are addressed in the embodiments described herein are not to be interpreted as limiting, but merely as a basis for the claims and as a representative basis for teaching one skilled in the art to variously employ the disclosed process and method.

The expression "MeI" is used herein as an abbreviation for methyl iodide. The expression "HI" is used herein as an abbreviation for hydrogen iodide. Unless specifically indicated otherwise, the expression "wt. %" as used herein refers to the percentage by weight of a particular component in the referenced composition. With respect to all ranges disclosed herein, such ranges are intended to include any combination of the mentioned upper and lower limits even if the particular combination is not specifically listed.

Embodiments of the disclosed process and system involve the production of acetic acid by carbonylating methanol in a carbonylation reaction. The carbonylation reaction may be represented by: $CH_3OH + CO \rightarrow CH_3COOH$.

Embodiments of the disclosed process generally include: (a) contacting a plurality of components in an acetic acid production system having a reactor and a first apparatus downstream thereof; and monitoring; and (b) determining a concentration of a first component in the reactor based on the respective concentrations of a second and a third component in the reactor and the temperature and pressure of the first apparatus. The following description elaborates upon the disclosed process.

Acetic Acid Reaction System

Figure 1:
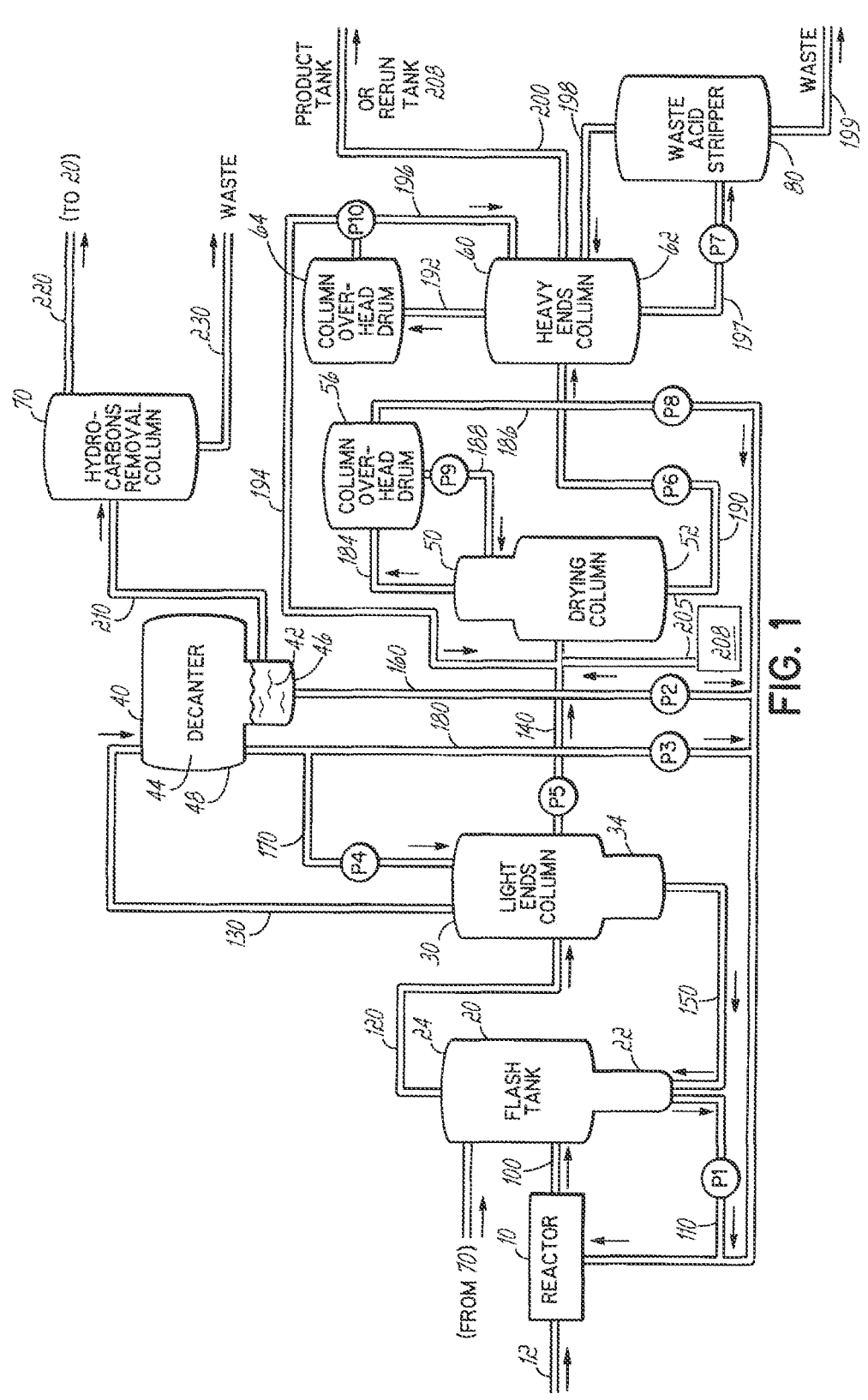
FIG. 1 is a schematic of an exemplary acetic acid production system in accordance with embodiments of the present techniques.

An exemplary acetic acid manufacturing plant practicing methanol carbonylation technology, as depicted schematically in FIG. 1, can be conveniently divided into three functional areas: reaction, light ends recovery, and purification. Acetic acid reaction systems may vary in the type and number of distillation columns, for example as described in U.S. Pat. Nos. 3,772,156, 4,039,395, 5,831,120, 5,227,520, 5,416,237 and 5,916,422, and in PCT publication WO98/22420, and such variations, which are within the skill of one of ordinary skill in the art, are included within the scope of this disclosure. In general, the reaction section consists of a reactor 10 and flash tank 20. The light ends recovery section consists of a light ends column 30 and a phase separation vessel 40 (decanter). The purification section consists also of the light ends column 30, as well as a drying column 50 and optionally a heavy ends column 60. The various columns and vessels are connected by transfer lines, such as pipes, through which the reaction system solutions flow, typically with the aid of pumps. For ease of depiction and discussion, the transfer lines and streams therein are referred to herein as one in the same, using the term "stream".

The feed to the reactor 10 is via stream 12 comprised of methanol, dimethyl ether, methyl acetate or mixtures thereof. Water may also be present in stream 12. Carbon monoxide or mixtures with inert gases are also fed to the process via stream 12. During normal reactor 10 operation, reactor contents are continuously withdrawn as a liquid. This is achieved by flashing reactor solution across a valve (not shown) to produce a vapor-liquid stream 100 which is sent to the flash tank 20 where vapor is separated from the liquid. The liquid, containing catalyst, accumulates in the bottom 22 of the flash tank 20 and is pumped back into the reactor 10 via stream 110 by a catalyst recycle pump P1. The vapor stream 120 leaving the top 24 of the flash tank 20 contains the acetic acid product, water, methyl iodide (MeI), hydrogen iodide (HI), and low levels of impurities, i.e. propionic acid and acetaldehyde. This vapor is fed to the light ends column 30. Thus, the primary purpose of the flash tank 20 is to separate the catalyst from the crude product and allow the catalyst to be returned to the reactor 10.

The light ends column 30 is critical to the overall process as it serves the dual purpose of crude acetic acid purification and of recycling iodide back to the reaction section. The light ends column 30 is fed from the overhead vapor stream 120 from the flash tank 20. It allows separation of the higher boiling acetic acid from the lower boiling components such as MeI and methyl acetate (MeOAc). Three streams 130, 140, 150 are removed from the light ends column 30. The overhead stream 130 consists primarily of MeI but also contains some water, MeOAc and acetic acid and is sent to a phase separator or decanter 40 described below. A sidedraw stream 140 from the light ends column 30 consists of wet acetic acid, which is sent to the drying column 50 by pump P5. The light ends bottoms stream 150 removed from bottoms 34 of light ends column 30 consists of water, HI and acetic acid, which are recycled to the reaction section, which encompasses the reactor 10 and flash tank 20.

The second part of the light ends recovery section is the phase separator 40, more commonly called the decanter. In this decanter 40, a heavy phase 42 consisting primarily of MeI and an immiscible light phase 44 consisting primarily of aqueous acetic acid are separated. The primary purpose of this separation of light phase 44 and heavy phase 42 is to recycle MeI to the reactor 10. The MeI to be recycled collects in a small boot 46 of the decanter 40, the volume of which is much less than that of the remaining top portion 48 of the decanter 40 which contains the light phase 44. The MeI in boot 46 is recycled to reactor 10 by pump P2 via bottoms stream 160. A secondary purpose of the light phase separation is to return by pump P4 via stream 170 some of the light phase 44 as reflux to the light ends column 30, the remainder of the light phase 44 being recycled via stream 180 to the reactor 10 by pump P3. The amount of light phase directed to stream 170 versus stream 180 can be adjusted by one or both of pumps P3 and P4.

Many acetic acid processes contain additional processing of the heavy phase 42 and the light phase 44. In processes such as those described in U.S. Pat. Nos. 4,102,922, 5,371, 286 and 5,599,976, the heavy phase 42 is further treated to remove alkanes. One such process is shown in FIG. 1 where the hydrocarbons removal column 70 is fed by a portion of the heavy phase 42 via stream 210. The overhead of the column 70 is returned via stream 220 to the flash tank 20. The alkanes-rich bottoms are sent to waste via stream 230. A number of acetic acid processes have additional treatments of the heavy phase 42 and light phase 44 to remove impurities such as acetaldehyde and its condensation products. Examples of such acetaldehyde removal systems are described in U.S. Pat. Nos. 5,599,976, 5,723,660, 5,625,095 and 5,783,731, EP Patent No. 487,284 and PCT Publication WO9817619. Various acetic acid process streams may be analyzed using embodiments of the present disclosure to provide improved control of the individual processing steps as well as overall process control.

Purification encompasses the light ends column 30, as discussed above, as well as a drying column 50 and heavy ends column 60. Many acetic acid processes contain an additional column 80 to strip acetic acid from higher boiling impurities. The drying column 50 is a large distillation column which takes as its feed a wet acetic acid stream 140 from the light ends column 30 through pump P5. As its name implies, the primary purpose of the drying column 50 is to remove water from the product acetic acid. Water is removed overhead via stream 184 to a column overhead drum 56 and returned to the reaction section via stream 186 by pump P8. A portion of the condensed solution in drum 56 is returned as column reflux via stream 188 by pump P9. In some acetic acid processes such as that described in U.S. Pat. Nos. 5,599,976 and 5,723,660, a portion of the overhead stream 184 condensed in drum 56 is added via transfer line (not shown) to either the light ends column 30 or drying column feed stream 140. The current disclosure offers improved process control of the processes described in the above patents. Dry acetic acid is removed from the bottoms 52 of the drying column 50 and is either pumped directly to product tanks (not shown) or to a heavy ends column 60 by pump P6 via stream 190 for further removal of impurities such as propionic acid. Additional acetic acid can be recovered from stream 197 which is fed to a waste acid stripper column 80 by pump P7. The recovered acetic acid is returned via stream 198 to heavy ends column 60. Waste propionic and higher acids are sent for disposal via stream 199. The overhead of heavy ends column 60 is sent via stream 192 to drum 64, condensed, and returned by pump P10 as reflux to the heavy ends column 60 via stream 196 or sent via stream 194 to be mixed with stream 140.

The purpose of the optional heavy ends column 60 is to remove higher boiling propionic acid impurity from acetic acid. The bottoms portion 62 of the heavy ends column 60 consists primarily of propionic acid while a sidedraw stream 200 consists of pure acetic acid which is sent to storage in a product tank. When sidedraw stream 200 is out of specification, stream 200 may be diverted to a rerun tank 208 rather than being sent to the product tank. When sidedrawn stream 200 is in specification it is sent to the product tank. The contents of rerun tank 208 may be reprocessed by introducing stream 205 to drying column 52. In some embodiments, stream 205 is combined with streams 140 and 194 prior to introduction into drying column 52.

In some aspects, methods for determining component concentrations are disclosed.

In some embodiments, the methods include providing a system configured for contacting a first component, a second component, and a third component, wherein the system includes a reactor, and a first apparatus downstream of the reactor.

The reactor generally may include any reactor known in the art. The reactor may include one or more inlets and one or more outlets that permit the reactor to be in fluid communication with one or more other apparatuses of a system, such as the first apparatus. The reactor may include a reservoir in which the first, second, and third components may be disposed, and the reactor may include one or more other features, including, but not limited to, a mixing apparatus, heater, etc.

The first apparatus downstream of the reactor may include any reservoir known in the art, such as a collection reservoir configured to collect a fluid of any one or more phases. In some embodiments, the first apparatus downstream of the reactor includes a flash tank. Other first apparatuses, however, are envisioned.

In some embodiments, the system also includes a second apparatus downstream of the reactor. Therefore, in some embodiments, the methods described herein include providing a system configured for contacting a first component, a second component, and a third component, wherein the system includes a reactor, a first apparatus downstream of the reactor, and a second apparatus downstream of the reactor. The second apparatus may be downstream of the first apparatus, or vice versa. The second apparatus may include a drying column.

The first component, the second component, and the third component may be selected independently from any reactant or non-reactant (e.g., solvent) of any known chemical process. In some embodiments, the first component is methyl acetate. In some embodiments, the second component is methyl iodide. In some embodiments, the third component is water.

In some embodiments, the methods described herein also include determining a concentration of the second component in the reactor; determining a concentration of the third component in the reactor; and determining a temperature and a pressure of (e.g., within) the first apparatus. The temperature and pressure of the first apparatus may be determined by any known techniques and/or equipment.

The methods described herein may include determining a concentration of the second component in a reactor, and determining a concentration of the third component in a reactor. The determining of the concentrations of the second and third components may be achieved by any direct or indirect analytical technique(s) known in the art or described herein, and the techniques used to determine the concentrations may be the same or different.

In some embodiments, the determining of the concentration of the second component in the reactor and the concentration of the third component in the reactor includes determining the concentration of the second component and the concentration of the third component in the reactor directly. In some embodiments, the determining of the concentration of the second component in the reactor and the concentration of the third component in the reactor includes determining the concentration of the second component and the concentration of the third component in the reactor directly via Fourier transform infrared spectroscopy and/or Raman spectroscopy.

In some embodiments, the determining of the concentration of the third component in the reactor includes determining a concentration of the third component in the second apparatus or in a feed provided to the second apparatus; and calculating the concentration of the third component in the reactor based on the concentration of the third component in (i) the second apparatus or (ii) the feed provided to the second apparatus. In some embodiments, the determining of the concentration of the second component in the reactor includes determining the concentration of the second component in the reactor directly, such as via Fourier transform infrared spectroscopy and/or Raman spectroscopy, and the determining of the concentration of the third component in the reactor includes determining a concentration of the third component in the second apparatus or in a feed provided to the second apparatus; and calculating the concentration of the third component in the reactor based on the concentration of the third component in (i) the second apparatus or (ii) the feed provided to the second apparatus.

In some embodiments, the second apparatus is a drying column, the third component is water, and the determining of the concentration of water in the drying column or the feed provided to the drying column includes determining the concentration of water via Fourier transform infrared spectroscopy and/or Raman spectroscopy. Determining of the concentration of water in the drying column or the feed provided to the drying column may be in accordance with a known method, such as those disclosed in U.S. Pat. No. 6,552,221, which is incorporated herein by reference. The drying column may be operated on a temperature gradient concept, and include a number of liquid loaded trays. On-line analysis of water in a drying column feed and/or in these trays could give an instantaneous and continually updated water profile of the column.

In some embodiments, the second apparatus is a drying column, the third component is water, and the determining of the concentration of water in the drying column or the feed provided to the drying column includes determining a light ends column (LEC) reflux ratio; and correlating the concentration of water according to Equations 2a and 2b:

$$[H_2O]_{DCf} = \frac{C_1 + C_2 T_{DCTy} + C_3(P_{DCovr} + dP_{DC}\left(\frac{x-y}{x}\right)}{C_4 + C_5\left(\frac{R_{DC}}{D_{DC}}\right) + C_6\left(\frac{D_{DC}}{F_{DC}}\right)}, \quad \text{(Eq. 2a)}$$

$$\text{and } [H_2O]_{LECT_s} = \frac{[H_2O]_{DCf}(F_{DC} + D_{HEC} + F_{rerun}) - }{[H_2O]_{HECd}D_{HEC} - [H_2O]_{rerun}F_{rerun}}{F_{DC}}, \quad \text{(Eq. 2b)}$$

wherein: $[H_2O]_{DCf}$ is the mass fraction of water in the drying column or feed provided to the drying column; $C_1$, $C_2$ and $C_3$ are drying column temperature profile coefficients; $T_{DCTy}$ is the drying column reactor water concentration correlation temperature at tray y; $P_{DCovr}$ is the drying column operating pressure; $dP_{DC}$ is the drying column total pressure drop from all trays; $C_4$, $C_5$ and $C_6$ are drying column mass transfer operating line coefficients; $R_{DC}$ is the drying column reflux rate; $D_{DC}$ is the drying column distillate rate; $F_{DC}$ is the drying column feed rate; $[H_2O]_{LECTs}$ is the light ends column sidedraw water concentration; $D_{HEC}$ is the heavy ends distillate rate; $F_{rerun}$ is the drying column feed rate from rerun tank; $[H_2O]_{HECd}$ is the heavy ends distillate water concentration; $D_{HEC}$ is the heavy ends distillate rate; and $[H_2O]_{rerun}$ is the rerun tank water concentration. The rerun tank, shown as 208 in FIG. 1, is an off-spec product tank from which off-spec acetic acid is returned to the drying column for re-processing. x and y respectively refer to the total number of drying column trays and the tray selected for the correlation.

As described herein at Example 2, units of measure for all equations and expressions in this example are in mass fraction "[H2O]", degrees Fahrenheit "T", psig "P, dP", and lbs/hr "F, D, R"; where all constants "C" are unitless.

In some embodiments, the calculating of the concentration of water in the reactor based on the concentration of the water in the second apparatus or the feed provided to the second apparatus includes solving Equation 3:

$$[H_2O]_{Reactor} \cong f\left\{[H_2O]_{LECT_s}, \frac{R_{LEC}}{D_{LEC}}\right\}, \quad \text{(Eq. 3)}$$

wherein: $[H_2O]_{Reactor}$ is the mass fraction of water in the reactor based on the concentration of water in the second apparatus of the feed thereto; $R_{LEC}$ is the light ends column reflux rate; and $D_{LEC}$ is the light ends column total distillate rate where the total refers to combined decanter light and heavy phase.

In some embodiments, the methods described herein include calculating a first concentration of the first component in the reactor based on (i) the concentration of the second component in the reactor, (ii) the concentration of the third component in the reactor, and (iii) the temperature and the pressure of the first apparatus.

As used herein, the phrase "first concentration of the first component" refers to a concentration of the first component that is calculated based on (i) the concentration of the second component in the reactor, (ii) the concentration of the third component in the reactor, and (iii) the temperature and the pressure of the first apparatus.

In some embodiments, the system also includes an analyzer configured to measure directly a second concentration of the first component in the reactor. Therefore, in some embodiments, the methods include providing a system configured for contacting a first component, a second component, and a third component, wherein the system includes a reactor, an analyzer configured to measure directly a second concentration of the first component in the reactor, and a first apparatus downstream of the reactor.

As used herein, the phrase "second concentration of the first component in the reactor" refers to a concentration of the first component in the reactor that is measured directly with an analyzer.

In some embodiments, the methods include directly measuring the second concentration of the first component with the analyzer. The analyzer may directly measure the second concentration of the first component by any known analytical technique. In some embodiments, the analyzer directly measures the second concentration of the first component via Fourier transform infrared spectroscopy and/or Raman spectroscopy.

The methods described herein may include comparing the first concentration of the first component and the second concentration of the first component. A result of the comparison may inform a further action. In some embodiments, the methods include replacing or repairing the analyzer if a difference between the first concentration and the second concentration of the first component exceeds a predetermined threshold. A predetermined threshold, for example, may include a percentage (e.g., 0.01% to 20%, 0.01%, to 15%, 0.01% to 10%, 0.01% to 5%, 0.01% to 1%, etc.) or a numerical value (e.g., within 20 units, 15 units, 10 units, 5 units, 1 unit, etc.). For example, if a predetermined threshold is 10%, then an analyzer could be replaced or repaired if the first concentration, as an arbitrary example, is 30 units and the second concentration is not within the range of 27 units to 33 units, or, in other words, 30 units±10%.

In some embodiments, the first component is methyl acetate, the second component is methyl iodide, the third component is water, the first apparatus is a flash tank, and the calculating of the first concentration of the first component in the reactor includes solving Equation 1:

$$[MeAc]_{Reactor} = \frac{T_{FlashTank} - C_w[H_2O]_{Reactor} + \frac{C_m([MeI]_{Reactor}) + C_pP_{FlashTank}}{C_a}}, \quad \text{(Eq. 1)}$$

wherein: [MeAc]Reactor is the reactor MeAc concentration; $T_{FlashTank}$ is the flash tank temperature; $C_w$ is the reactor water coefficient; $[H_2O]_{Reactor}$ is the reactor $H_2O$ concentration; $C_m$ is the reactor MeI coefficient; $[MeI]_{Reactor}$ is the reactor MeI concentration; $C_p$ is the flash tank operating pressure coefficient; $P_{FlashTank}$ is the flash tank pressure; and $C_a$ is the flash tank temperature coefficient.

As explained at Example 1, the units of measure in Equation 1 are mass fraction of total reactor composition, degrees Fahrenheit, and psig; and all constants "C" are unitless. Those skilled in the art will recognize that the numerical value of coefficients, otherwise known as constants, will vary from manufacturer to manufacturer and will be specific to variables including, but not limited to, distillation train design and reactor chemistry.

In some embodiments, the method comprises providing a system configured for contacting a first component, a second component, and third component, wherein the system includes a reactor, and a first apparatus downstream of the reactor, and determining a first concentration of the first component in the reactor based on (i) the concentration of the second component in the reactor, (ii) the concentration of the third component in the reactor, and (iii) the temperature and the pressure of the first apparatus.

Figure 2:
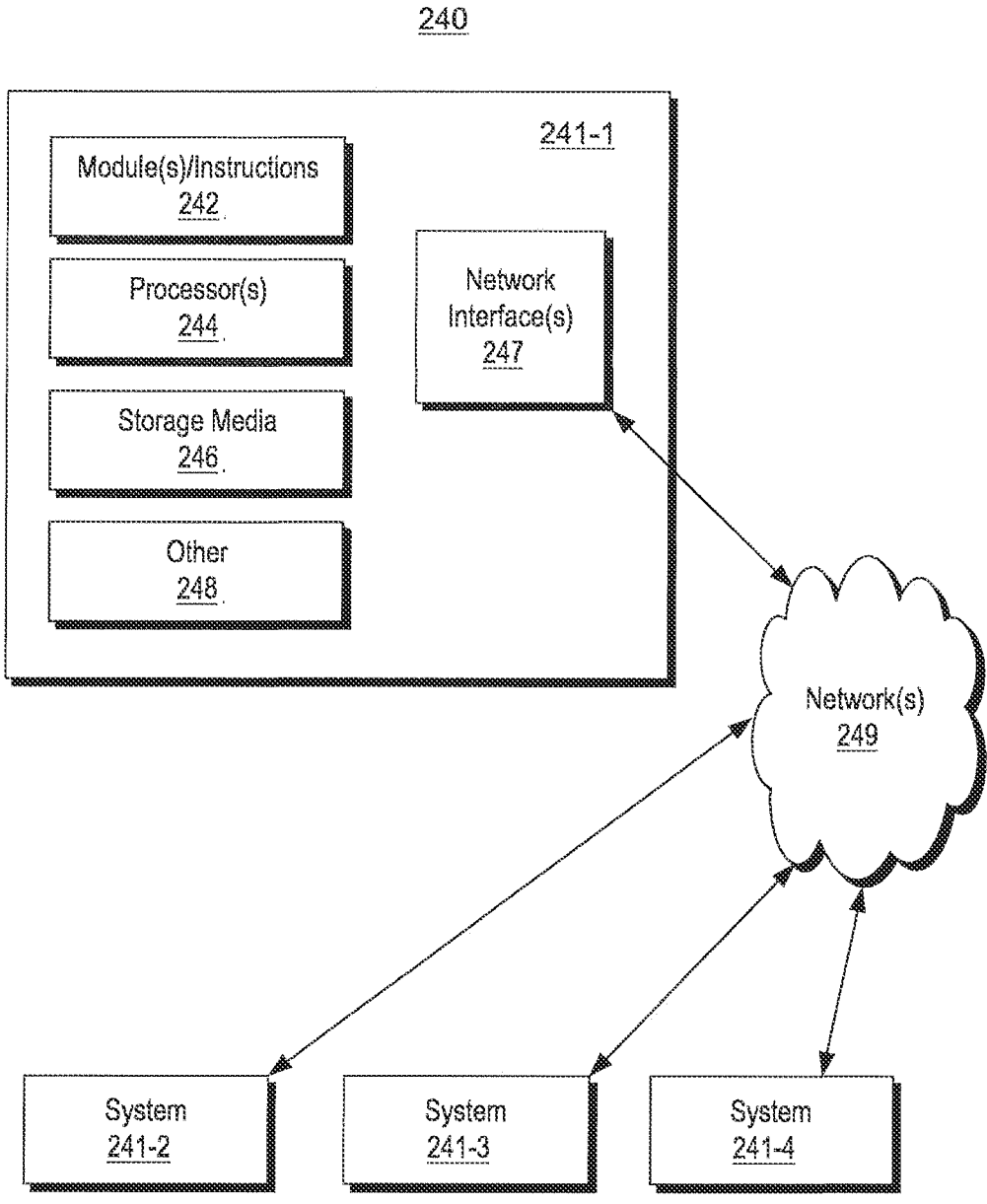
FIG. 2 illustrates examples of computing and networking equipment.

In some embodiments, method(s) of the present disclosure may be executed by a computing system. FIG. 2 shows an example of a system 240 that can include one or more computing systems 241-1, 241-2, 241-3 and 241-4, which may be operatively coupled via one or more networks 249, which may include wired and/or wireless networks.

As an example, a system can include an individual computer system or an arrangement of distributed computer systems. In the example of FIG. 2, the computer system 241-1 can include one or more modules 242, which may be or include processor-executable instructions, for example, executable to perform various tasks (e.g., receiving information, requesting information, processing information, simulation, outputting information, etc.). For example, execution of such instructions may cause the processor(s) to implement one or more portions and/or embodiments of the method(s) described above.

As an example, a module may be executed independently, or in coordination with, one or more processors 244, which is (or are) operatively coupled to one or more storage media 246 (e.g., via wire, wirelessly, etc.). As an example, one or more of the one or more processors 244 can be operatively coupled to at least one of one or more network interface 247. In such an example, the computer system 241-1 can transmit and/or receive information, for example, via the one or more networks 249 (e.g., consider one or more of the Internet, a private network, a cellular network, a satellite network, etc.).

As an example, the computer system 241-1 may receive from and/or transmit information to one or more other devices, which may be or include, for example, one or more of the computer systems 241-2, etc. A device may be located in a physical location that differs from that of the computer system 241-1. As an example, a location may be, for example, a processing facility location, a data center location (e.g., server farm, etc.), a chemical facility, a reactor, a flash tank, a light ends column, a heavy ends column, a drying column, etc. As an example, a device may be, for example, a temperature sensor, a pressure sensor, a spectrometer, a Fourier transform infrared spectrometer, a Raman spectrometer, etc.

As an example, a processor may be or include a microprocessor, microcontroller, processor module or subsystem, programmable integrated circuit, programmable gate array, or another control or computing device.

As an example, the storage media 246 may be implemented as one or more computer-readable or machine-readable storage media. As an example, storage may be distributed within and/or across multiple internal and/or external enclosures of a computing system and/or additional computing systems.

As an example, a storage medium or storage media may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories, magnetic disks such as fixed, floppy and removable disks, other magnetic media including tape, optical media such as compact disks (CDs) or digital video disks (DVDs), BLUERAY® disks, or other types of optical storage, or other types of storage devices.

As an example, a storage medium or media may be located in a machine running machine-readable instructions, or located at a remote site from which machine-readable instructions may be downloaded over a network for execution.

As an example, various elements of a system such as, for example, a computer system, may be implemented in hardware, software, or a combination of both hardware and software (e.g., including firmware), including one or more signal processing and/or application specific integrated circuits.

As an example, a system may include a processing apparatus that may be or include a general purpose processors or application specific chips (e.g., or chipsets), such as ASICs, FPGAs, PLDs, or other appropriate devices.

Figure 3:
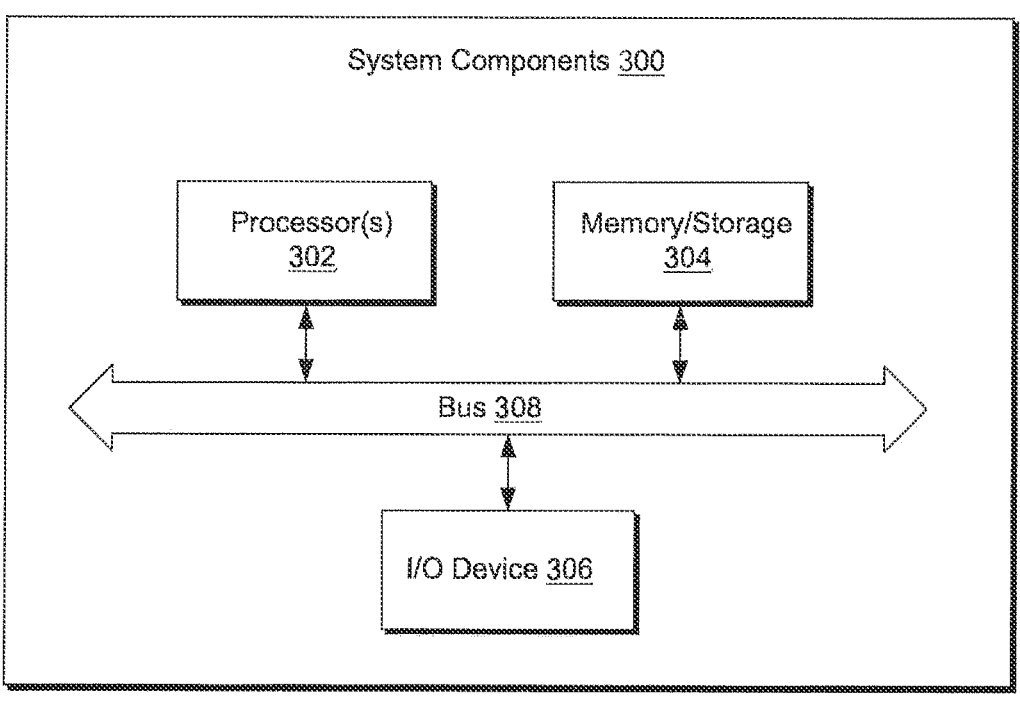
FIG. 3 illustrates example elements of a system and a networked system.
Figure 3:
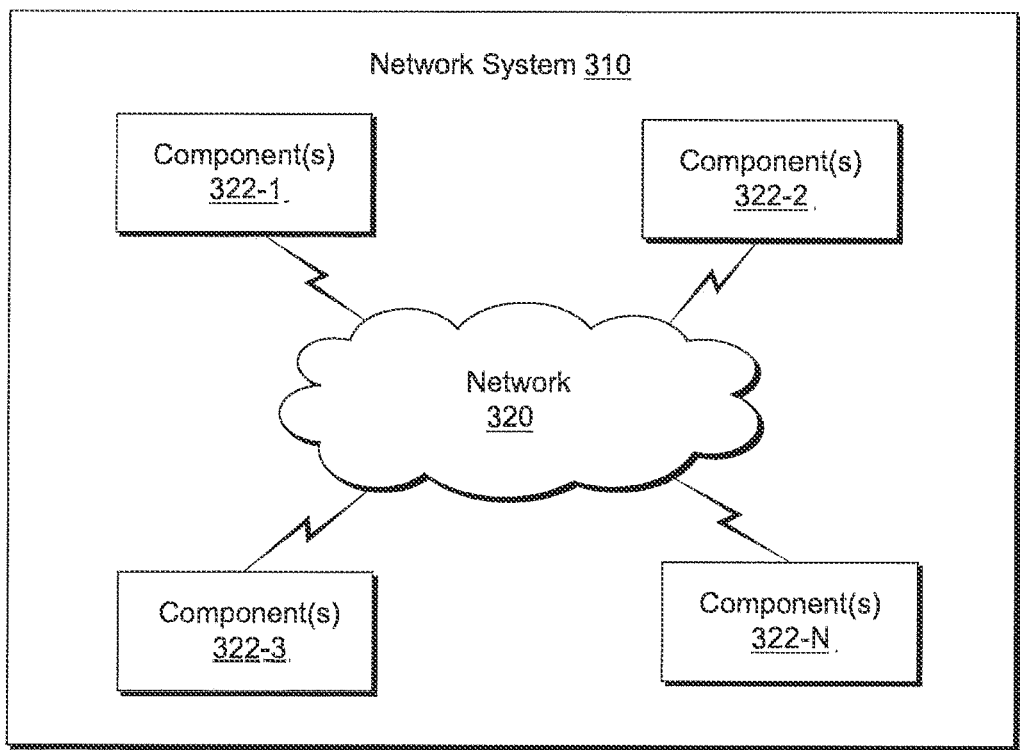

FIG. 3 shows elements of a computing system 300 and a networked system 310. The system 300 includes one or more processors 302, memory and/or storage elements 304, one or more input and/or output devices 306 and a bus 308. In an example embodiment, instructions may be stored in one or more computer-readable media (e.g., memory/storage elements 304). Such instructions may be read by one or more processors (e.g., the processor(s) 302) via a communication bus (e.g., the bus 308), which may be wired or wireless. The one or more processors may execute such instructions to implement (wholly or in part) one or more attributes (e.g., as part of a method). A user may view output from and interact with a process via an I/O device (e.g., the device 306). In an example embodiment, a computer-readable medium may be a storage element such as a physical memory storage device, for example, a chip, a chip on a package, a memory card, etc. (e.g., a computer-readable storage medium)

In an example embodiment, elements may be distributed, such as in the network system 310. The network system 310 includes elements 322-1, 322-2, 322-3, . . . 322-N. For example, the elements 322-1 may include the processor(s) 302 while the element(s) 322-3 may include memory accessible by the processor(s) 302. Further, the element(s) 322-2 may include an I/O device for display and optionally interaction with a method. The network may be or include the Internet, an intranet, a cellular network, a satellite network, etc. For example, one or more of the elements 322-N may also include, for example, a temperature sensor, a pressure sensor, a spectrometer, a Fourier transform infrared spectrometer, a Raman spectrometer, etc. For example, the I/O device may receive and display an alarm should the difference between the first concentration and second concentration of the first component exceed a predetermined threshold. The alarm may indicate that the analyzer requires maintenance or replacement.

As an example, an I/O device may be a mobile device that includes one or more network interfaces for communication of information. For example, a mobile device may include a wireless network interface (e.g., operable via IEEE 802.11, ETSI GSM, BLUETOOTH®, satellite, etc.). As an example, a mobile device may include elements such as a main processor, memory, a display, display graphics circuitry (e.g., optionally including touch and gesture circuitry), a SIM slot, audio/video circuitry, motion processing circuitry (e.g., accelerometer, gyroscope), wireless LAN circuitry, smart card circuitry, transmitter circuitry, GPS circuitry, and a battery. As an example, a mobile device may be configured as a cell phone, a tablet, etc. As an example, a method may be implemented (e.g., wholly or in part) using a mobile device. As an example, a system may include one or more mobile devices.

As an example, a system may be a distributed environment, for example, a so-called "cloud" environment where various devices, elements, etc. interact for purposes of data storage, communications, computing, etc. As an example, a device or a system may include one or more elements for communication of information via one or more of the Internet (e.g., where communication occurs via one or more Internet protocols), a cellular network, a satellite network, etc. As an example, a method may be implemented in a distributed environment (e.g., wholly or in part as a cloud-based service).

As an example, information may be input from a display (e.g., consider a touchscreen), output to a display or both. As an example, information may be output to a projector, a laser device, a printer, etc. such that the information may be viewed.

The terms "a," "an," and "the" are intended to include plural alternatives, e.g., at least one. For instance, the disclosure of "a reactor," "an apparatus," and the like, is meant to encompass one, or mixtures or combinations of more than one reactor, apparatus, and the like, unless otherwise specified.

In the descriptions provided herein, the terms "includes," "is," "containing," "having," and "comprises" are used in an open-ended fashion, and thus should be interpreted to mean "including, but not limited to." When methods or systems are claimed or described in terms of "comprising" various components or steps, the methods or systems can also "consist essentially of" or "consist of" the various components or steps, unless stated otherwise.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, numerical end points of ranges disclosed herein are approximate.

Throughout this application, the term "about" is used to indicate that a value includes a variation of error, such as for the device, the method being employed to determine the value, or the variation that exists among the study subjects. The term "about" is used to imply the natural variation of conditions and represent a variation of plus or minus 5% of a value. In some embodiments, the variation is plus or minus 1% of a value.

The processes described herein may be carried out or performed in any order as desired in various implementations. Additionally, in certain implementations, at least a portion of the processes may be carried out in parallel. Furthermore, in certain implementations, less than or more than the processes described may be performed.

Although the disclosed process and system have been described in detail, it should be understood that various changes, substitutions and alterations can be made herein without departing from the spirit and scope of the invention as defined by the appended claims. Moreover, the scope of the present application is not intended to be limited to the particular embodiments of the processes, machines, compositions, means, methods, and/or steps described in the specification. As one of the ordinary skill in the art will readily appreciate from the present disclosure, processes, machines, compositions, means, methods, and/or steps, presently existing or later to be developed that perform substantially the same function or achieve substantially the same result as the corresponding embodiments described herein, may be utilized according to the present invention. Accordingly, the appended claims are intended to include within their scope such processes, machines, compositions, means, methods, and/or steps.

EXAMPLES

The present disclosure is further illustrated by the following examples, which are not to be construed in any way as imposing limitations upon the scope thereof. On the contrary, it is to be understood that resort may be had to various other aspects, embodiments, modifications, and equivalents thereof which, after reading the description herein, may suggest themselves to one of ordinary skill in the art without departing from the spirit of the present disclosure or the scope of the appended claims. Thus, other aspects will be apparent to those skilled in the art from consideration of the specification and practice of the subject matter disclosed herein.

Example 1—Methyl Acetate Measurement

In this example, methyl acetate concentration was determined in a reactor containing methyl acetate, methyl iodide, and water.

As the methyl acetate calculation of this example required real time reactor methyl iodide and water values, reasonably accurate values of these two components were available from spectroscopic data, but other techniques could be used.

The reactor methyl iodide had a strong, fully-resolved Raman peak, while water had a partially overlapped Raman peak.

In the method of this example, a combination of Raman methyl iodide and water values, and flash tank temperature and pressure values were used to calculate reactor methyl acetate concentration for a period in which a feed rate cut was happening.

Figure 4:
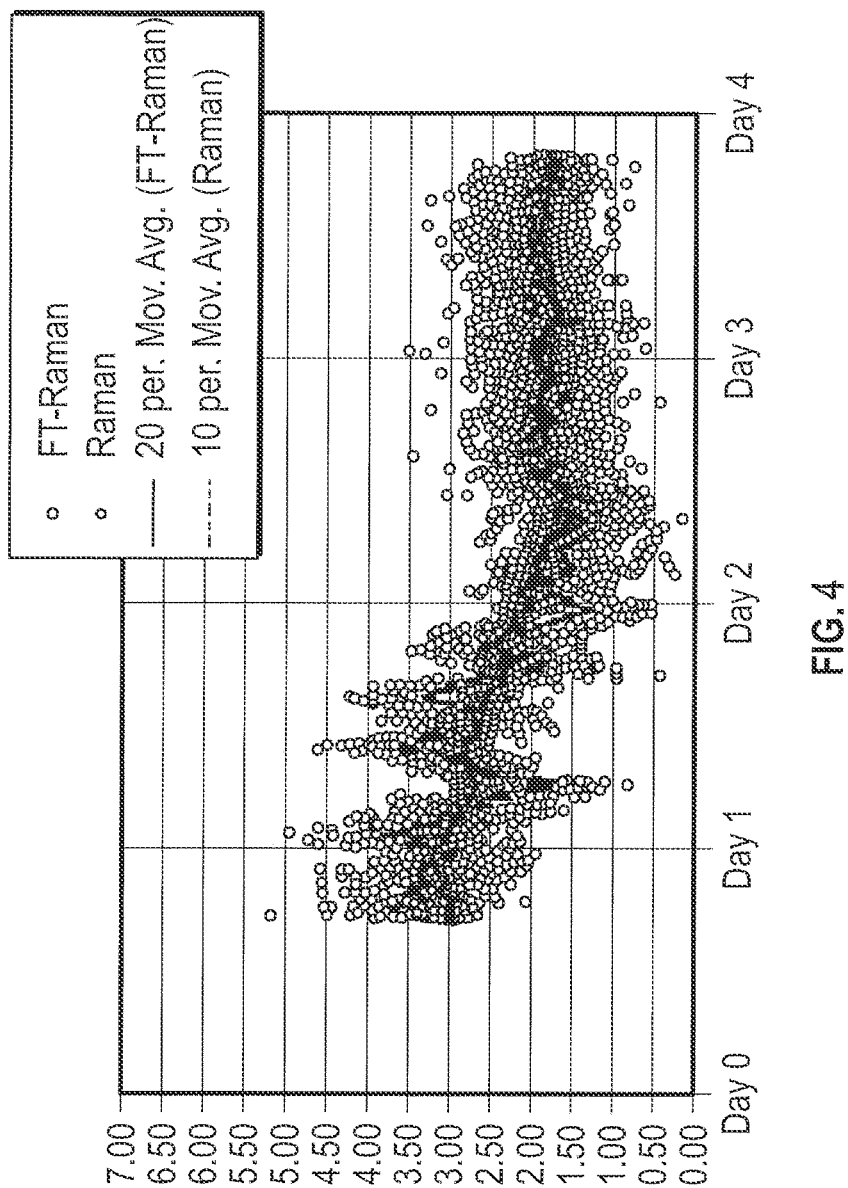
FIG. 4 depicts overlaid plots of methyl acetate concentration (i) measured by Raman spectroscopy and (ii) predicted by correlation with Raman composition inputs.

The calculated values of this example were overlaid with Raman-measured values in the plot of FIG. 4. The FT-Raman-labelled trend line contained the calculated methyl acetate values, while the Raman-labelled trend line contained the Raman-measured methyl acetate values.

FIG. 4 demonstrates that there was a strong correlation between the trends. The calculated methyl acetate concentration was noisier (i.e., it was slightly less precise) than the Raman-measured trend, with the source of the noise being the Raman water measurement, which factored into the methyl acetate calculation.

Nevertheless, the data indicated the usefulness of a calculated methyl acetate trend as a cross-check of Raman data or as the primary source of methyl acetate data when, for example, a Raman analyzer is down.

The following Equation 1 provided the methyl acetate calculation used in this example:

$$[MeAc]_{Reactor} = \frac{\begin{array}{c} T_{FlashTank} - C_w[H_2O]_{Reactor} + \\ C_m([MeI]_{Reactor} + C_{m2}^*) + C_pP_{FlashTank} \end{array}}{C_a}. \quad \text{(Eq. 1)}$$

The units of measure in Equation 1 were mass fraction of total reactor composition, degrees Fahrenheit, and psig;

where all constants "C" were unitless. This correlation was based on the fact that the adiabatic flash primary components composition depended strictly on temperature and pressure.

Example 2—Measurement Using Drying Column Feed (DCF) H₂0 Data

The method of Example 1 may be performed in an alternative manner, as explained in this example. Instead of using Raman reactor water data, drying column feed water data may be used to infer reactor water composition. The drying column feed water data may be available from either (i) a correlation using process data from a drying column, or (ii) a near infrared (e.g., NIR FTIR) analyzer when available.

Drying column water concentration can correlate strongly with reactor water concentration (with an offset) where the only contributing variable may be the light ends column reflux ratio, which can be a key plant independent variable.

In this example, drying column feed water composition was correlated using Equation 2a and 2b as follows:

$$[H_2O]_{DCf} = \frac{C_1 + C_2 T_{DCTy} + C_3(P_{DCovr} + dP_{DC}\left(\frac{x-y}{x}\right)}{C_4 + C_5\left(\frac{R_{DC}}{D_{DC}}\right) + C_6\left(\frac{D_{DC}}{F_{DC}}\right)}, \quad \text{(Eq. 2a)}$$

$$\text{and } [H_2O]_{LECT6} = \frac{[H_2O]_{DCf}(F_{DC} + D_{HEC} + F_{rerun}) -}{F_{DC}} \\ \frac{[H_2O]_{HECd}D_{HEC} - [H_2O]_{rerun}F_{rerun}}{F_{DC}}. \quad \text{(Eq. 2b)}$$

The conceptual correlation from drying column feed water to reactor water, for this example, is depicted at Equation 3 below:

$$[H_2O]_{Reactor} \cong f\left\{[H_2O]_{LECT_s}, \frac{R_{LEC}}{D_{LEC}}\right\}. \quad \text{(Eq. 3)}$$

Units of measure for all equations and expressions in this example were in mass fraction "[H₂0]", degrees Fahrenheit "T", psig "P, dP", and lbs/hr "F, D, R"; where all constants "C" were unitless.

The basis of the water correlations of this example was the vapor-liquid equilibrium of a water-acetic acid system from a pressure compensated temperature inside the separation equipment that was then adjusted based on changes to the separation unit's mass balance.

Figure 5:
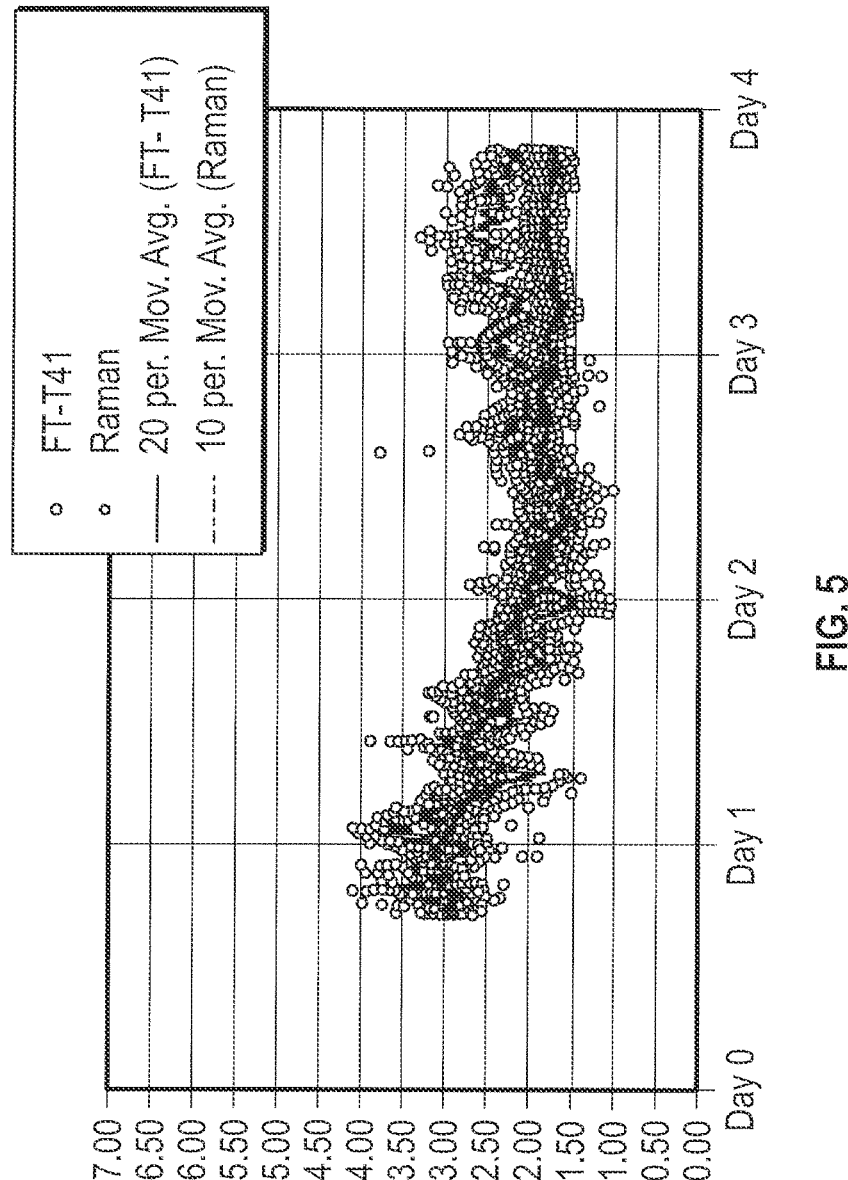
FIG. 5 depicts overlaid plots of methyl acetate concentration (i) measured by Raman spectroscopy and (ii) predicted using a methyl iodide concentration measured by Raman spectroscopy, and correlated water concentration.

When reactor water values obtained from the drying column feed correlation (Equations 2a, 2b, and 3) were used for reactor methyl acetate calculations, the calculated methyl acetate trend line had significantly less noise (FIG. 5) compared to the previously examined case in which Raman measured reactor water values were used for the calculation. FIG. 5 depicts Raman reactor methyl acetate data overlaid with the reactor methyl acetate predicted by the correlation, with Raman methyl iodide and correlated water as inputs.

Also possible is the real time measurement of drying column feed water data with an NIR-FTIR analyzer. Unlike the partially resolved peak in Raman, water has several fully resolved peaks in NIR. Therefore, NIR water and correlated data have the benefit of improved accuracy based on a fully resolved FTIR peak, and lack of noise from temperature and pressure instrumentation, respectively.

The particular embodiments disclosed above are illustrative only, as the process and system may be modified and practiced in different but equivalent manners apparent to those skilled in the art having the benefit of the teachings herein. In the event of conflict between one or more of the incorporated patents or publications and the present disclosure, the present specification, including definitions, controls. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

The invention claimed is:

1. A method for measuring component concentration, the method comprising:
    providing a system configured for contacting a first component, a second component, and a third component, the system comprising
    a reactor, and
    a first apparatus downstream of the reactor;
    determining a concentration of the second component in the reactor;
    determining a concentration of the third component in the reactor;
    determining a temperature and a pressure of the first apparatus; and
    calculating a first concentration of the first component in the reactor based on (i) the concentration of the second component in the reactor, (ii) the concentration of the third component in the reactor, and (iii) the temperature and the pressure of the first apparatus, wherein
    the first component is methyl acetate,
    the second component is methyl iodide,
    the third component is water,
    the first apparatus is a flash tank, and
    the calculating of the first concentration of the first component in the reactor comprises solving Equation 1:

$$[MeAc]_{Reactor} = \frac{T_{FlashTank} - C_w[H_2O]_{Reactor} +}{C_a} \frac{C_m([MeI]_{Reactor}) + C_p P_{FlashTank}}{C_a} \quad \text{(Eq. 1)}$$

wherein: $[MeAc]_{Reactor}$ is the reactor MeAc concentration; $T_{FlashTank}$ is the flash tank temperature; $C_w$ is the reactor water coefficient; $[H_2O]_{Reactor}$ is the reactor $H_2O$ concentration; $C_m$ is the reactor MeI coefficient; $[MeI]_{Reactor}$ is the reactor MeI concentration; $C_p$ is the flash tank operating pressure coefficient; $P_{FlashTank}$ is the flash tank pressure; and $C_a$ is the flash tank temperature coefficient.

2. The method of claim 1, wherein the system further comprises an analyzer configured to measure directly a second concentration of the first component in the reactor.

3. The method of claim 2, further comprising directly measuring the second concentration of the first component with the analyzer via Fourier transform infrared spectroscopy and/or Raman spectroscopy.

4. The method of claim 3, further comprising generating an alarm if a difference between the first concentration and the second concentration of the first component exceeds a predetermined threshold.

5. The method of claim 4, further comprising replacing or repairing the analyzer if a difference between the first concentration and the second concentration of the first component exceeds a predetermined threshold.

6. The method of claim 1, wherein the determining of the concentration of the second component in the reactor comprises determining the concentration of the second component in the reactor directly via Fourier transform infrared spectroscopy and/or Raman spectroscopy.

7. The method of claim 1, wherein the determining of the concentration of the second component in the reactor and the concentration of the third component in the reactor comprises determining the concentration of the second component and the concentration of the third component in the reactor directly via Fourier transform infrared spectroscopy and/or Raman spectroscopy.

8. The method of claim 1, wherein the first component is methyl acetate, the second component is methyl iodide, and the third component is water.

9. The method of claim 1, wherein the first apparatus is a flash tank.

10. The method of claim 1, wherein the system further comprises a second apparatus downstream of the reactor.

11. The method of claim 10, wherein the determining of the concentration of the third component in the reactor comprises determining a concentration of the third component in the second apparatus or in a feed provided to the second apparatus; and calculating the concentration of the third component in the reactor based on the concentration of the third component in (i) the second apparatus or (ii) the feed provided to the second apparatus.

12. The method of claim 11, wherein the second apparatus is a drying column, and the third component is water.

13. The method of claim 12, wherein the determining of the concentration of water in the drying column or the feed provided to the drying column comprises determining the concentration of water via Fourier transform infrared spectroscopy and/or Raman spectroscopy.

14. The method of claim 12, wherein the determining of the concentration of water in the drying column or the feed provided to the drying column comprises— determining a light ends column (LEC) reflux ratio; and correlating the concentration of water according to Equations 2a and 2b:

$$[H_2O]_{DCf} = \frac{C_1 + C_2 T_{DCTy} + C_3(P_{DCovr} + dP_{DC}\left(\frac{x-y}{x}\right)}{C_4 + C_5\left(\frac{R_{DC}}{D_{DC}}\right) + C_6\left(\frac{D_{DC}}{F_{DC}}\right)}, \quad \text{(Eq. 2a)}$$

$$\text{and } [H_2O]_{LECT_s} = \frac{[H_2O]_{DCf}(F_{DC} + D_{HEC} + F_{rerun}) - [H_2O]_{HECd}D_{HEC} - [H_2O]_{rerun}F_{rerun}}{F_{DC}} \quad \text{(Eq. 2b)}$$

wherein: $[H_2O]_{DCf}$ is the mass fraction of water in the drying column or feed provided to the drying column; $C_1$, $C_2$ and $C_3$ are drying column temperature profile coefficients; $T_{DCTy}$ is the drying column reactor water concentration correlation temperature at tray y; $P_{DCovr}$ is the drying column operating pressure; $dP_{DC}$ is the drying column total pressure drop from all trays; $C_4$, $C_5$ and $C_6$ are drying column mass transfer operating line coefficients; $R_{DC}$ is the drying column reflux rate; $D_{DC}$ is the drying column distillate rate; $F_{DC}$ is the drying column feed rate; $[H_2O]_{LECTs}$ is the light ends column sidedraw water concentration; $D_{HEC}$ is the heavy ends distillate rate; $F_{rerun}$ is the drying column feed rate from rerun tank; $[H_2O]_{HECd}$ is the heavy ends distillate water concentration; $D_{HEC}$ is the heavy ends distillate rate; and $[H_2O]_{rerun}$ is the rerun tank water concentration.

15. The method of claim 14, wherein the calculating of the concentration of water in the reactor based on the concentration of the water in the second apparatus or the feed provided to the second apparatus comprises solving Equation 3:

$$[H_2O]_{Reactor} \cong f\left\{[H_2O]_{LECT_s}, \frac{R_{LEC}}{D_{LEC}}\right\} \quad \text{(Eq. 3)}$$

wherein: $[H_2O]_{Reactor}$ is the mass fraction of water in the reactor based on the concentration of water in the second apparatus of the feed thereto; $[H_2O]_{LECTs}$ is the light ends column sidedraw water concentration; $R_{LEC}$ is the light ends column reflux rate; and $D_{LEC}$ is the light ends column total distillate rate where the total refers to combined decanter light and heavy phase.

* * * * *